(12) United States Patent
Kandel et al.

(10) Patent No.: US 8,441,639 B2
(45) Date of Patent: May 14, 2013

(54) METROLOGY SYSTEMS AND METHODS

(75) Inventors: Daniel Kandel, Aseret (IL); Vladimir Levinski, Nazereth Ilia (IL); Alexander Svizher, Haifa (IL); Joel Seligson, Misgav (IL); Andrew Hill, San Jose, CA (US); Ohad Bachar, Timrat (IL); Amnon Manassen, Haifa (IL); Yung-Ho Alex Chuang, Cupertino, CA (US); Ilan Sela, Haifa (IL); Moshe Markowitz, Haifa (IL); Daria Negri, Nesher (IL); Efraim Rotem, Hod Hasharon (IL)

(73) Assignee: KLA-Tencor Corp., Milpitas, CA (US)

( * ) Notice: Subject to any disclaimer, the term of this patent is extended or adjusted under 35 U.S.C. 154(b) by 320 days.

(21) Appl. No.: 12/872,988

(22) Filed: Aug. 31, 2010

(65) Prior Publication Data

US 2011/0069312 A1    Mar. 24, 2011

Related U.S. Application Data

(60) Provisional application No. 61/239,699, filed on Sep. 3, 2009.

(51) Int. Cl.
*G01J 4/00* (2006.01)
*G01B 11/14* (2006.01)
*G01B 11/28* (2006.01)
*G01B 11/04* (2006.01)
*G01B 11/00* (2006.01)

(52) U.S. Cl.
USPC ........... 356/369; 356/399; 356/625; 356/630; 356/636

(58) Field of Classification Search ....................... None
See application file for complete search history.

(56) References Cited

U.S. PATENT DOCUMENTS

| | | | |
|---|---|---|---|
| 4,710,642 A | 12/1987 | McNeil |
| 4,999,014 A | 3/1991 | Gold et al. |
| 5,042,951 A | 8/1991 | Gold et al. |
| 5,159,412 A | 10/1992 | Willenborg et al. |
| 5,164,790 A | 11/1992 | McNeil et al. |
| 5,181,080 A | 1/1993 | Fanton et al. |
| 5,241,369 A | 8/1993 | McNeil et al. |
| 5,309,276 A | 5/1994 | Rodgers |
| 5,412,473 A | 5/1995 | Rosencwaig et al. |
| 5,674,652 A | 10/1997 | Bishop et al. |
| 5,703,692 A | 12/1997 | McNeil et al. |
| 5,739,909 A | 4/1998 | Blayo et al. |
| 5,830,611 A | 11/1998 | Bishop et al. |
| 5,859,424 A | 1/1999 | Norton et al. |

(Continued)

FOREIGN PATENT DOCUMENTS

| | | |
|---|---|---|
| DE | 19925831 | 12/2000 |
| EP | 1628164 | 2/2006 |
| WO | 2004/010121 | 1/2004 |

OTHER PUBLICATIONS

Wein, Steven et al. "Gaussian-apodized apertures and small-angle scatter measurement," Optical Engineering, vol. 28, No. 3, pp. 273-280, Mar. 1989.*

(Continued)

*Primary Examiner* — Gordon Stock, Jr.
(74) *Attorney, Agent, or Firm* — Ann Marie Mewherter (57) ABSTRACT

Various metrology systems and methods are provided.

22 Claims, 1 Drawing Sheet

U.S. PATENT DOCUMENTS

| | | |
|---|---|---|
| 5,867,276 A | 2/1999 | McNeil et al. |
| 5,963,329 A | 10/1999 | Conrad et al. |
| 6,104,486 A | 8/2000 | Arimoto |
| 6,323,946 B1 | 11/2001 | Norton |
| 6,429,943 B1 | 8/2002 | Opsal et al. |
| 6,628,381 B1 | 9/2003 | Komem et al. |
| 6,678,046 B2 | 1/2004 | Opsal |
| 6,690,473 B1 * | 2/2004 | Stanke et al. ............ 356/601 |
| 6,704,661 B1 | 3/2004 | Opsal et al. |
| 6,801,315 B2 | 10/2004 | Finarov et al. |
| 6,801,358 B2 | 10/2004 | Shafer et al. |
| 6,813,034 B2 | 11/2004 | Rosencwaig et al. |
| 6,819,426 B2 | 11/2004 | Sezginer et al. |
| 6,891,627 B1 | 5/2005 | Levy et al. |
| 7,095,504 B1 | 8/2006 | Ames et al. |
| 7,145,654 B2 * | 12/2006 | Norton ..................... 356/369 |
| 7,242,477 B2 | 7/2007 | Mieher et al. |
| 7,511,830 B2 | 3/2009 | Fabrikant et al. |
| 7,515,253 B2 | 4/2009 | Bareket et al. |
| 7,528,941 B2 | 5/2009 | Kandel et al. |
| 7,541,201 B2 | 6/2009 | Ghinovker |
| 7,616,313 B2 | 11/2009 | Kandel et al. |
| 7,663,753 B2 | 2/2010 | Mieher et al. |
| 2002/0018217 A1 | 2/2002 | Weber-Grabau et al. |
| 2006/0033921 A1 | 2/2006 | Den Boef et al. |
| 2006/0066855 A1 | 3/2006 | Den Boef et al. |
| 2006/0290931 A1 * | 12/2006 | Zhao et al. ................ 356/369 |
| 2008/0129986 A1 | 6/2008 | Phillip |
| 2008/0273662 A1 | 11/2008 | Wenbing et al. |

OTHER PUBLICATIONS

International Preliminary Report on Patentability for PCT/US10/47539 mailed on Mar. 15, 2012.

International Search Report and Written Opinion for PCT/US10/47539 mailed on Apr. 26, 2011.

"Mask Overlay Determination," IBM Technical Disclosure Bulletin, Dec. 1978, pp. 2772-2773.

Extended European Search Report for European Application No. 10814430.4 mailed Feb. 20, 2013.

* cited by examiner

METROLOGY SYSTEMS AND METHODS

CROSS-REFERENCE TO RELATED APPLICATIONS

This application claims priority to U.S. patent application Ser. No. 61/239,699 entitled "Multifunction Metrology System," filed Sep. 3, 2009, which is incorporated by reference as if fully set forth herein.

BACKGROUND OF THE INVENTION

1. Field of the Invention

The present invention generally relates to metrology systems and methods.

2. Description of the Related Art

The following description and examples are not admitted to be prior art by virtue of their inclusion in this section.

Metrology processes are performed on wafers at various points in a semiconductor manufacturing process to determine a variety of characteristics of the wafers such as a width of a patterned structure on the wafer, a thickness of a film formed on the wafer, and overlay of patterned structures on one layer of the wafer with respect to patterned structures on another layer of the wafer. Optical critical dimension (CD) metrology is currently performed using either spectroscopic scatterometry or angle-resolved scatterometry. Optical overlay metrology is performed using either imaging methods or scatterometry-based methods (both spectroscopic and angle-resolved). Film metrology is performed using spectroscopic ellipsometry. An example of a spectroscopic ellipsometer is illustrated in U.S. Pat. No. 5,859,424 to Norton et al., which is incorporated by reference as if fully set forth herein.

However, the currently used metrology methods described above have a number of disadvantages. For example, currently optical CD metrology methods are limited to larger grating target sizes (e.g., 50 microns by 50 microns). Similarly, scatterometry-based overlay methods are limited in the minimum grating cell size to 15 microns by 15 microns. Another disadvantage of the old methods are that scatterometry-based overlay metrology and imaging-based overlay metrology are implemented on totally separate platforms.

Accordingly, it may be advantageous to develop metrology methods and systems that do not have one or more of the disadvantages described above.

SUMMARY OF THE INVENTION

The following description of various embodiments is not to be construed in any way as limiting the subject matter of the appended claims.

One embodiment relates to a metrology system. The metrology system includes a light source configured to produce a diffraction-limited light beam. The metrology system also includes an apodizer configured to shape the light beam in the entrance pupil of illumination optics in such a way, that the irradiance farther than 1.5 microns from the center of an illumination spot in the wafer plane is less than $10^{-6}$ of the peak irradiance of the center of the spot. In addition, the metrology system includes optical elements configured to direct the diffraction-limited light beam from the apodizer to the illumination spot on a grating target on a wafer and to collect scattered light from the grating target. The metrology system further includes a field stop configured to reject a portion of the collected scattered light. The metrology system also includes a detector configured to detect the scattered light that passes through the field stop and to generate output responsive to the detected scattered light such that the grating target is measured by the metrology system using scatterometry. In addition, the metrology system includes a computer system configured to determine a characteristic of the grating target using the output. The metrology system may be further configured as described herein.

Another embodiment relates to a metrology method. The metrology method includes shaping a diffraction-limited light beam in the entrance pupil of illumination optics in such a way that the irradiance farther than 1.5 microns from the center of an illumination spot in the wafer plane is less than $10^{-6}$ of the peak irradiance of the center of the spot. The metrology method also includes directing the diffraction-limited light beam to the illumination spot on a grating target on a wafer. In addition, the metrology method includes collecting scattered light from the grating target. The metrology method further includes rejecting a portion of the collected scattered light from the grating target. The method also includes detecting the scattered light subsequent to rejecting the portion of the collected scattered light. In addition, the method includes generating output responsive to the detected scattered light. The method further includes determining a characteristic of the grating target using the output.

Each of the steps of the method described above may be performed as described further herein. The method described above may include any other step(s) of any other method(s) described herein. The method described above may be performed using any of the systems described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and will be described herein in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1:
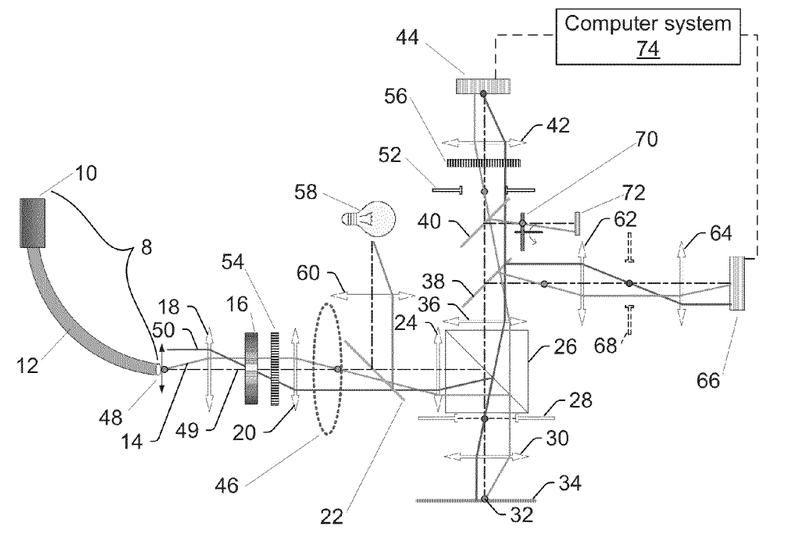
FIG. 1 is a schematic diagram illustrating a side view of an embodiment of a metrology system.

Turning now to the drawings, it is noted that the FIGURE is not drawn to scale. In particular, the scale of some of the elements of the FIGURE is greatly exaggerated to emphasize characteristics of the elements.

One embodiment relates to a metrology system. The metrology system (or "metrology tool") is intended for use in semiconductor device production and related applications. The various metrology tasks described further herein can be performed in various phases of semiconductor or related device production such as lithography and etch. In some embodiments, the metrology systems described herein may be integrated into a semiconductor fabrication system such as a lithography system or an etch system or any other system that alters the wafer physically, chemically, or mechanically in some manner. The metrology system may be integrated into the semiconductor fabrication system such that the metrology system can measure the wafer and determine a characteristic of the wafer during a step of a process performed on the wafer by the semiconductor fabrication system and/or before a step, after a step, or between steps of a process performed on the wafer by the semiconductor fabrication system without removing the wafer from the semiconductor fabrication system (i.e., while the wafer is disposed within the semiconductor fabrication system). Examples of how the metrology system may be integrated into a semiconductor fabrication system are described and illustrated in commonly owned U.S. Pat. No. 6,891,627 to Levy et al., which is incorporated by reference as if fully set forth herein.

FIG. 1 illustrates one embodiment of the metrology system. The metrology system includes a light source configured to produce a diffraction-limited light beam. In one embodiment, the light source includes a laser and a single-mode fiber. In this manner, the illumination beam may be generated by using a laser through a single-mode fiber as the source. For example, as shown in FIG. 1, light source 8 may include laser 10 and single-mode fiber 12 that generates diffraction-limited light beam 14. Such a light source enables an illumination spot (and possibly a diffraction-limited illumination spot), which together with the apodizer described further herein enables metrology of relatively small targets. The light source may generate light having only one wavelength (i.e., monochromatic light), light having a number of discrete wavelengths (i.e., polychromatic light), or light having multiple wavelengths (i.e., broadband light). The light generated by the light source may have any suitable wavelength(s) such as visible wavelength(s) or any wavelength(s) between about 190 nm to about 900 nm. The light source may include any other suitable light source such as a white light source, an ultraviolet (UV) laser, an arc lamp, a laser-driven light source such as the EQ-1000 that is commercially available from Energetiq Technology, Inc., Woburn, Mass., a supercontinuum laser (broadband laser) such as the Koheras Versa commercially available from NKT Photonics Inc., Morganville, N.J., or some combination thereof. The light source may also be configured to provide light having sufficient brightness, which in some cases may be a brightness greater than about 1 W/(nm cm$^2$ Sr). The metrology system may also include a fast feedback to the light source for stabilizing its power and wavelength. The fast feedback to the light source may be configured as described further herein.

The metrology system also includes an apodizer configured to shape the light beam in the entrance pupil of illumination optics in such a way that the irradiance farther than 1.5 microns from the center of an illumination spot in the wafer plane is less than $10^{-6}$ of the peak irradiance of the center of the spot. For example, as shown in FIG. 1, the metrology system may include apodizer 16 positioned in the path of the diffraction-limited light beam generated by the light source. The apodizer may be positioned in the illumination pupil of the metrology system. Apodization can be generally defined as altering the light distribution in the entrance pupil of an optical system (e.g., using a mask to alter the amplitude and/or phase of the illumination beam) thereby changing the intensity profile of the illumination beam. In the present case, the apodizer is configured to reduce irradiance in the "tails" of the illumination spot (e.g., portions of the illumination spot greater than 1.5 microns from the center of the illumination spot) to less than $10^{-6}$ of the peak irradiance thereby reducing the so-called signal contamination. Including such an apodizer in the metrology systems described herein is one of the features that may enable metrology on relatively small grating targets.

The metrology system further includes optical elements configured to direct the light beam from the apodizer to the illumination spot on a grating target on a wafer and to collect scattered light from the grating target. For example, in the embodiment shown in FIG. 1, the optical elements may include refractive optical elements 18 and 20, beam splitter 22, refractive optical element 24, beam splitter 26, objective 30 with its aperture stop 28, refractive optical element 36, beam splitters 38 and 40, and refractive optical element 42. Refractive optical elements 18, 20, 24, 36, and 42 may include any suitable refractive optical elements known in the art such as refractive lenses. In addition, although refractive optical elements 18, 20, 24, 36, and 42 are illustrated schematically in FIG. 1 in the same manner using the same conventional notation, all, some, or none of the refractive optical elements may be configured the same or differently. Furthermore, each of refractive optical elements 18, 20, 24, 36, and 42 may include one or more refractive optical elements.

Refractive optical element 18 is configured to direct the diffraction-limited light beam from light source 8 to apodizer 16. Refractive optical element 20 is configured to direct the light beam from the apodizer through beam splitter 22, which may include a dichroic beam splitter, to refractive optical element 24. Refractive optical element 24 is configured to direct the light beam to beam splitter 26, which may include any suitable beam splitter. Beam splitter 26 is configured to reflect the light beam from refractive optical element 24 to objective 30, which is configured to focus the diffraction-limited light beam to illumination spot 32 on a grating target (not shown) on wafer 34. Objective 30 may include any suitable refractive optical element(s) and/or any suitable reflective optical element(s). For example, the objective may have an all-reflective design or a catadioptric design such as those described in U.S. Pat. Nos. 5,309,276 to Rodgers and 6,801,358 to Shafer et al., which are incorporated by reference as if fully set forth herein. The objective may also be designed for wavelengths from about 150 nm to about 1000 nm. In addition, the objective may be designed to have no central obscuration in the illumination.

The objective (or "objective lens") may be a relatively high-numerical aperture (NA) objective lens (e.g., having an NA of about 0.9 or greater), thereby enabling optimized selection of the illumination pupil (pupil area selection not shown herein). A relatively high NA objective as that term is used herein generally means that the semi-diameter of the entrance pupil of the objective is comparable to the focal length of the objective, or in other words, the rays emanating from the objective onto the wafer fill a relatively large cone angle. For example, an objective with an NA of 0.9 has an entrance pupil semi-diameter of 0.9 f, where f is the focal length of the lens. This is equivalent to the fact that the maximum cone angle of the rays hitting the wafer is arcsin 0.9=64 degrees. Therefore, relatively high-NA objective lenses have relatively large entrance pupils. In this manner, different portions (e.g., only one portion of the entrance pupil) may be used for illumination. In other words, the fact that the entrance pupil (used here as the illumination pupil) is relatively large enables selective illumination of sub-areas of this pupil, which then translates into sub-cones of the maximum illuminating cone provided by the overall objective lens NA.

Pupil area selection may be performed using any suitable optical elements that can be used to direct light from a light source to only certain portions of the illumination pupil. For example, optical elements (not shown) may be used to modulate the light source to thereby select a portion of the illumination pupil that is used for measurements performed by the metrology system. Examples of suitable optical elements that can be used to spatially modulate the light include a reflective micromirror array device, such as are available from Texas Instruments, Dallas, Tex., a diffractive micromirror array device, such as are available from Fraunhofer Institute, Dresden, Germany, a liquid crystal device (LCD), a diffractive optical element, fixed apertures, any other optical element(s) that can perform spatial modulation of light, or some combination thereof. Alternatively, optical elements (not shown) may be used in place of selecting only a portion or portions of the illumination pupil for use in the measurements performed by the metrology system.

Refractive optical elements 18 and 20, beam splitter 22, refractive optical element 24, beam splitter 26, and objective 30, therefore, form an illumination subsystem (or "illumination optics") of the metrology system that is configured to direct light from the light source to the wafer (e.g., for scatterometry measurements). In this manner, the illumination subsystem may be used for scatterometry measurements, and the diffraction-limited light beam in the illumination subsystem as shown encircled and indicated by reference numeral 46 may be a Gaussian beam. For example, the light source of the metrology system may be configured to provide a Gaussian beam, and the apodizer may not alter the Gaussian nature of the diffraction-limited light beam.

Objective 30 is also configured to collect light from the wafer. The light collected from the wafer includes scattered light. However, the light collected from the wafer may also include other light from the wafer (e.g., reflected light). Objective 30 directs the collected light through beam splitter 26 to refractive optical element 36, which directs the collected light through beam splitters 38 and 40 to refractive optical element 42. Refractive optical element 42 is configured to direct the collected scattered light to detector 44. Detector 44 may be configured as described further herein. In this manner, objective 30, beam splitter 26, refractive optical element 36, beam splitters 38 and 40, refractive optical element 42, and detector 44 form a detection subsystem of the metrology system. The detection subsystem may be used for scatterometry measurements as described further herein.

Optical aberration specifications for the objective may be derived from the scatterometry spot size described further herein. For example, the design and manufacture of the objective lens for an angle-resolved scatterometry implementation of the metrology system are preferably performed to ensure the above-mentioned substantially low irradiance at the illumination spot tails. The optical design preferably ensures a minimal amount of ghosting that may result from the relatively strong wafer reflection reflecting back to the wafer from any of the optical surfaces of the objective. The design also preferably provides for oversized apertures for minimizing scattering from lens edges and air-spaces of at least 1 mm for reducing coherence effects. Scattering from the illumination is preferably further minimized by assuring relatively low surface roughness on optical surfaces and coatings (typically about 0.1 nm root mean squared (RMS)) as well as relatively low surface defectivity (scratch and dig, similar to 5/1X0.040 and L1X0.006 per ISO 10110). Apertures and stops included in the metrology system preferably have carefully manufactured edges for minimal scattering into the wafer, and the internal mechanical surfaces of the objective lens assembly are preferably machined and treated to absorb any scattered light. The optical elements are preferably cleaned and assembled in a clean environment to keep the number of dust particles on the optical elements to below a level that will cause appreciable scattering. Therefore, the embodiments described herein may have specifications for the optical manufacturing requirements for surface roughness, scratch and dig, defects, and cleanliness for ensuring relatively low stray light and in this way relatively low residual irradiance. Considerations similar to those described above for the objective lens are preferably applied to all optical elements included in the metrology system. Such optical manufacturing requirements for relatively low stray light may be combined with any other embodiments described herein.

In one embodiment, the illumination spot on the grating target has a diameter that is less than 3 microns. For example, as described above, residual irradiance is established as a performance criterion for critical dimension (CD) and overlay metrology from grating targets, residual irradiance is the irradiance outside of a 1.5 micron radius from the center of the illumination spot on the wafer, and the residual irradiance limit is $10^{-6}$ of the irradiance at the center of the illumination spot. Therefore, the illumination spot may have a radius of approximately 1.5 microns and therefore a diameter that is approximately 3 microns or less.

In another embodiment, the metrology system is configured to scan the illumination spot across the grating target while the scattered light from the grating target is being collected. For example, as shown in FIG. 1, the metrology system may be configured to laterally scan diffraction-limited light beam 14 in directions 48, for example, by laterally moving the light source to thereby move the diffraction-limited light beam. In this manner, the metrology system may field scan the illumination spot across a grating target. The metrology system may scan the spot in a raster or other fashion across the grating target area. The metrology system may be configured to use any suitable device(s) (e.g., a mechanical stage) to scan the illumination spot across the grating target. In this manner, rather than providing an extended illumination spot on the target, the spot may be scanned within the grating target area. (The position of light beam 14 shown in FIG. 1 represents light rays through the center of the field of the optical system, while the position of light beam 50 is different to represent light rays through the center of the pupils of the optical system. The dots along optical axis 49 of the metrology system represent the points at which the different rays represented by light beams 14 and 50 intersect the optical axis.)

In this manner, the metrology system embodiments described herein enable measurements on grating targets that are smaller than the grating targets currently used for scatterometry measurements. For example, in some embodiments, the grating target has lateral dimensions of less than 10 microns by less than 10 microns. The lateral dimensions are defined in a plane substantially parallel to the upper surface of the wafer. In one such example, the grating target may have lateral dimensions of 5 microns by 5 microns. For example, the embodiments described herein enable substantially accurate optical measurement of CD from relatively small grating targets (e.g., 5 microns×5 microns). In addition, the embodiments described herein enable substantially accurate optical scatterometry overlay measurements from relatively small grating cells (e.g., 5 microns×5 microns). In this manner, one advantage of the embodiments described herein is that the metrology system configuration enables optical CD metrology on grating targets as small as 5 microns by 5 microns and scatterometry-based overlay metrology on grating targets of cell size as small as 5 microns by 5 microns. The grating targets themselves may include any suitable grating targets known in the art.

In one embodiment, the optical elements are configured to concentrate ghost images of the collected scattered light to localized areas in an imaging pupil of the optical elements or to spread the ghost images out across the imaging pupil to reduce irradiance of the ghost images. For example, the embodiments described herein may be configured using an optical design principle for the pupil imaging system, which either concentrates ghost images, which are coherent to the signal, to specific localized areas in the pupil image, such as the pupil center within a radius of, for instance, 0.1 NA, or spreads them over a sufficiently large area to minimize the ghost irradiance to, for instance, less than $10^{-6}$ of the signal. Such pupil ghost image control may be applied in combination with any of the other embodiments described herein.

The metrology system also includes a field stop configured to reject a portion of the collected scattered light. For example, in one embodiment, the metrology system includes field stop 52 positioned in a path of the collected scattered light such that the field stop can reject a portion of the collected scattered light. In this manner, the collection field stop is used in the collection arm for scatterometry (e.g., angle-resolved scatterometry). The collection field stop is a possible enabler for relatively small scatterometry metrology targets by providing an optimized balance between the rejection of unwanted signals around the target and sufficient pupil resolution. For example, the field stop size may be optimized, for a given grating target size, for the tradeoffs between signal contamination and pupil imaging resolution.

The metrology system may be configured to perform a method for aligning the field stop to a metrology grating target. Aligning the field stop to a metrology grating target may be performed using spot illumination and aligning the various components to this spot. For example, the illumination spot in the plane of an illumination field stop may be observed, and the illumination field stop may be aligned to this spot. A mirror wafer (or other suitable reflective surface) may be brought into focus under the objective. The reflected illumination spot in the plane of the collection field stop may be observed, and the collection field stop may be aligned to this spot. The illumination spot on the wafer may be observed through separate alignment optics (e.g., using detector 66 and the corresponding optical elements described further herein), and these optics may be aligned to the spot. When the metrology grating target is brought into the field of view, detector 66 and its corresponding optical elements may be used to bring the target into the location of the illumination spot thereby aligning the field stop to the metrology grating targets.

In one embodiment, the field stop is not centered on an optical axis along which the collected scattered light travels to thereby reduce ghosting of the collected scattered light on the detector described further herein. For example, an optional implementation of the field stop is that of offsetting the field stop from the optical axis. Such positioning of the field stop is an additional strategy for reducing ghosting. In particular, an off-axis field stop may be used for reducing, and even minimizing, signal contamination due to ghosting. In this manner, design and manufacture of the entire optical system up to the collection field stop (including the use of an apodizer to suppress the tails of the optical signal at the edges of the collection field stop) may be performed to assure minimal levels of scattering and ghosting.

In addition, the metrology system includes a detector configured to detect the scattered light that passes through the field stop and to generate output responsive to the detected scattered light such that the grating target is measured by the metrology system using scatterometry. For example, detector 44 may be configured to detect the scattered light that passes through field stop 52 and to generate output responsive to the detected scattered light such that the grating target is measured by the metrology system using scatterometry. The detector may include any suitable detector such as a charge coupled device (CCD). In this manner, the light source (e.g., laser 10 and single-mode fiber 12) described above may be used as a scatterometry light source and the detector may be used as the scatterometry metrology detector. In some embodiments, the metrology system may be configured to collect the scatterometric signals from a 5 micron by 5 micron metrology target with an illumination spot of 0.6 microns in diameter by scanning the spot in a raster or other fashion across the target area and collecting signals serially from consecutive scan points.

In one embodiment, the scatterometry includes angle-resolved scatterometry. In this manner, the metrology system may be configured as an angle-resolved scatterometer. In other words, the metrology system may be configured to measure the intensity of the scattered light at multiple discrete angles. Such measurements may be performed sequentially (one discrete angle after another), e.g., by moving one or more optical elements between measurements, or simultaneously, by separately measuring the intensity of the scattered light at multiple discrete angles within the collection space using a single detector or more than one detector. In addition, such an embodiment of the metrology system may be combined with features of any other embodiment(s) described herein. For example, the angle-resolved scatterometer embodiment may be combined with a field stop configured as described herein while at the same time concentrating the unwanted pupil ghosts to a localized pupil area. In another embodiment, the scatterometry includes angle-resolved scatterometry performed using multiple discrete wavelengths. The metrology system may be configured to perform angle-resolved scatterometry using several discrete wavelengths either concurrently (in parallel) or sequentially one after the other. Such measurements may be performed in a number of different ways known in the art. The metrology system may also be configured to perform angle-resolved scatterometry using several discrete wavelengths either concurrently (in parallel) or sequentially one after the other and using fast feedback for stabilizing the light source power and wavelength. In addition, as described further herein, the optical elements may include a polarizer and analyzer that can be used to perform measurements in more than one polarization state. For example, in one embodiment, the metrology system may be configured to perform angle-resolved scatterometry using several discrete wavelengths either concurrently (in parallel) or sequentially one after the other, combined with the use of several polarization states either concurrently (in parallel) or sequentially one after the other. Such measurements may be performed in a number of different ways known in the art. In addition, the metrology system may be configured to perform angle-resolved scatterometry using several discrete wavelengths either concurrently (in parallel) or sequentially one after the other, combined with the use of several polarization states either concurrently (in parallel) or sequentially one after the other and using fast feedback for stabilizing light source power and wavelength.

In an additional embodiment, the scatterometry includes spectroscopic scatterometry. Spectroscopic scatterometry may be performed using the metrology system in a number of different ways known in the art. In a further embodiment, the scatterometry includes spectroscopic scatterometry performed using multiple discrete angles. Spectroscopic scatterometry using multiple discrete angles may be performed using the metrology system embodiments in a number of different ways known in the art. The metrology system may be configured to perform spectroscopic scatterometry using several discrete angles either concurrently (in parallel) or sequentially one after the other. In addition, the metrology system may be configured to perform spectroscopic scatterometry using several discrete angles either concurrently (in parallels or sequentially one after the other, combined with the use of several polarization states either concurrently (in parallel) or one after the other. Such measurements may be performed in a number of different ways known in the art. Furthermore, the scatterometry may be either spectroscopic scatterometry or angle-resolved scatterometry or a combination of both spectroscopic scatterometry and angle-resolved scatterometry.

In one embodiment, the optical elements include a polarizer positioned in the path of the diffraction-limited light beam and an analyzer positioned in the path of the collected scattered light. For example, as shown in FIG. 1, the optical elements may include polarizer 54 positioned in the path of the diffraction-limited light beam and analyzer 56 positioned in the path of the collected scattered light. In one such embodiment, the polarizer and the analyzer are configured such that the scatterometry can be performed using multiple polarization states. For example, the polarizer and the analyzer may be configured such that if the polarizer and analyzer are rotated, the polarizer and analyzer will impart different polarizations to the diffraction-limited light beam and collected scattered light, respectively. Therefore, the metrology system may rotate the polarizer and/or analyzer depending on the polarization state(s) being used for the measurements. The polarizer and the analyzer may include any suitable polarizing components known in the art.

In another such embodiment, the metrology system is configured to use at least the light source, the optical elements including the polarizer and the analyzer, and the detector to perform ellipsometry measurements of the wafer. The ellipsometry measurements may be performed using the metrology system embodiments in any manner known in the art. The ellipsometry measurements may include single wavelength ellipsometry measurements, spectroscopic ellipsometry measurements, variable angle ellipsometry measurements, variable angle spectroscopic ellipsometry measurements, any other ellipsometry measurements, or some combination thereof.

In some embodiments, the metrology system includes an additional detector configured to generate an image of the wafer. In this manner, the metrology system may be configured for imaging-based metrology measurements of the wafer. For example, in the embodiment shown in FIG. 1, the metrology system includes additional light source 58, which may include any suitable light source. The light source may generate light having only one wavelength (i.e., monochromatic light), light having a number of discrete wavelengths (i.e., polychromatic light), or light having multiple wavelengths (i.e., broadband light). The light generated by the light source may have any suitable wavelength(s) such as UV wavelength(s). The light source may be further configured as described with respect to light source 8. Furthermore, although the metrology system is shown in FIG. 1 as including two light sources, one for scatterometry or other metrology measurements and another for imaging, the metrology system may include only one light source that can be used for all of the measurements described herein including scatterometry and other metrology measurements as well as imaging.

The metrology system may also include refractive optical element 60, which is configured to direct light from additional light source 58 to beam splitter 22. Refractive optical element 60 may be further configured as described herein. Beam splitter 22 is configured to reflect light from refractive optical element 60 to refractive optical element 24, which directs the light to beam splitter 26. The light from the additional light source is reflected by beam splitter 26 through objective 30, which focuses the light on the wafer.

Light reflected by the wafer is collected by objective 30, which directs the collected reflected light through beam splitter 26 to refractive optical element 36. Refractive optical element 36 directs the collected reflected light to beam splitter 38, which reflects the collected reflected light to refractive optical element 62. Refractive optical element 62 directs the collected reflected light to refractive optical element 64, which focuses the collected reflected light to additional detector 66. Refractive optical elements 62 and 64 may be configured as described herein. The additional detector is configured to generate an image of the wafer using the collected reflected light. The additional detector may include any suitable detector such as a CCD. The imaging detector may be used for imaging-based metrology as described further herein. In addition, the metrology system may be further configured for two-beam imaging. For example, the metrology system may be configured to perform two-beam imaging as described in commonly owned U.S. Pat. No. 7,528,941 to Kandel et al., which is incorporated by reference as if fully set forth herein. In such embodiments, the optical aberration specifications for the objective may be derived as described above (e.g., for scatterometry spot size requirements) in combination with a two-beam imaging tool-induced shift (TIS) error budget. Furthermore, the imaging detector may be used for navigation of the wafer with respect to the optical elements (e.g., such that the grating target on the wafer may be moved into the field of view of the optical elements by using images of the wafer generated by the additional detector). In this manner, the metrology system embodiments described herein may include a combination of scatterometry and imaging subsystems on the same platform, where scatterometry can be either spectroscopic scatterometry or angle-resolved scatterometry or a combination of both.

The optical elements that can be used to generate an image of the wafer may be used or complemented by other optical elements in such a way that the image of the exit pupil of the optical system becomes accessible. In this manner, one or more optical elements such as aperture 68 can be positioned in the plane of the pupil image. As such, an option for accessing the pupil image is provided.

The metrology system may include other optical elements. For example, as shown in FIG. 1, beam splitter 40 may be configured to allow a portion of the collected scattered light to pass through the beam splitter and may reflect another portion of the collected scattered light. The reflected portion of the collected scattered light may be used to determine the focus of the metrology system. For example, the reflected portion of the collected scattered light may be directed to focus detection chopper 70, which may include any suitable chopper. Light that passes through focus detection chopper 70 may be detected by detector 72. Detector 72 may be configured to generate output in response to the light detected by the detector. Detector 72 may include any suitable detector such as a CCD. A computer system such as that described further herein may be configured to determine if the grating target or film being measured on the wafer is in focus using the output generated by detector 72 in any suitable manner. The metrology system may include one or more devices (not shown) such as a stage that is configured to move the wafer or one or more optical elements of the metrology system if the grating target or the film is determined to be out of focus.

As described above, the metrology system shown in FIG. 1 includes a number of detectors configured to detect the light from the wafer and to generate output responsive to the detected light such that the grating target can be measured by the metrology system using a number of different techniques. The metrology system shown in FIG. 1 may also include additional detectors. For example, the metrology system may include a spectrometer (not shown) configured to detect the light from the wafer and to generate output responsive to the detected light. The spectrometer may include any suitable spectrometer. Light scattered from the wafer may be directed to the spectrometer by a beam splitter (not shown) positioned in the path of the collected scattered light. The beam splitter may be configured as described further herein. Any other suitable optical elements may also be positioned in a path of the light detected by the spectrometer. The spectrometer may be configured to measure an intensity of the scattered light as a function of wavelength. In this manner, the metrology system may be configured to perform measurements of the wafer using spectroscopic scatterometry. The metrology system shown in FIG. 1, therefore, may include a combination of scatterometry and imaging systems on the same platform, where scatterometry can be either spectroscopic scatterometry or angle-resolved scatterometry, or a combination of both. Furthermore, one of the detectors shown in FIG. 1 may be configured as or replaced with a spectrometer. For example, beam splitter 38 may reflect a portion of the collected scattered light to detector 66 shown in FIG. 1, and detector 66 may be configured as or replaced with a spectrometer that is configured as described above.

The metrology system further includes a computer system configured to determine a characteristic of the grating target using the output. For example, as shown in FIG. 1, the metrology system includes computer system 74 that is configured to determine a characteristic of the grating target using the output generated by detector 44. In this manner, the computer system may be configured to use output from the detector responsive to scattered light to determine a characteristic of the grating target. In addition, the computer system may be configured to determine a characteristic of the grating target using the output from detector 66. In this manner, the computer system may be configured to use output from the detector responsive to reflected light or an image of the wafer to determine a characteristic of the grating target. The computer system may determine the characteristic of the grating target using any suitable method(s), algorithm(s), model(s), technique(s), etc. known in the art.

Computer system 74 is coupled to detectors 44 and 66 (e.g., by one or more transmission media shown by the dashed lines in FIG. 1, which may include any suitable transmission media known in the art) such that the computer system may receive the output generated by the detectors. The computer system may be coupled to each of the detectors in any suitable manner. In addition, the computer system may be coupled to any other detectors included in the metrology system in a similar manner. Computer system 74 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

In one embodiment, the characteristic includes CD of patterned structures in the grating target. The computer system may determine the CD of the patterned structures (and other characteristics of the patterned structures) using scatterometry measurements as described in commonly assigned U.S. Pat. No. 7,511,830 to Fabrikant et al., which is incorporated by reference as if fully set forth herein, or in any other suitable manner. In this manner, the embodiments described herein may combine an apodizer, a field stop, and a relatively small grating target for optical CD metrology. In another embodiment, the characteristic includes overlay of patterned structures in the grating target with respect to patterned structures of another grating target formed on the wafer. The grating target and the other grating target are formed on different layers of the wafer. The computer system may be configured to determine overlay using the output responsive to the collected scattered light as described in commonly owned U.S. Pat. No. 7,616,313 to Kandel et al. and U.S. Pat. No. 7,663,753 to Mieher et al., which are incorporated by reference as if fully set forth herein, or in any other suitable manner. In this manner, the embodiments described herein may combine an apodizer, a field stop, and a set of relatively small grating targets for scatterometry overlay metrology. In addition, the embodiments described herein may combine an apodizer, a field stop, relatively small grating targets, and pupil imaging for CD and overlay metrology. Furthermore, the embodiments described herein may combine an apodizer, a field stop, relatively small grating targets, pupil imaging, and discrete illumination spectral lines in the visible and near-UV or deep-UV for CD and overlay metrology. In addition, as described above, the scatterometry may include spectroscopic scatterometry. The CD and overlay of the grating target may be determined using spectroscopic scatterometry measurements of the grating target.

In one embodiment described further above, the metrology system includes an additional detector configured to generate an image of the wafer. In one such embodiment, the computer system is configured to determine an additional characteristic of the grating target using the image. The computer system may be configured to determine the additional characteristic of the grating target using the image and any suitable method(s), algorithm(s), technique(s), model(s), and the like. In some such embodiments, the characteristic includes scatterometry-based overlay, and the additional characteristic includes imaging-based overlay. The computer system may be configured to determine imaging-based overlay in any suitable manner. For example, the computer system may be configured to determine overlay using imaging as described in commonly owned U.S. Pat. No. 7,541,201 to Ghinovker, which is incorporated by reference as if fully set forth herein. As such, the embodiments described herein enable both scatterometry-based and imaging-based overlay metrology on a single platform.

In additional such embodiments, the optical elements include an objective lens configured to collect the scattered light from the grating target and configured to collect light from the wafer used to generate the image. For example, as shown in FIG. 1, the optical elements may include objective 30 that is configured to collect the scattered light from the grating target and configured to collect light from the wafer used to generate the image. In this manner, the angle-resolved scatterometry objective and imaging overlay objective may be the same optical element(s). However, another option is to implement two separate objective lenses (not shown), one for angle-resolved scatterometry, and the other for imaging overlay. If the metrology system includes two such separate objective lenses, the metrology system may be configured to move the optics depending upon the measurements to be performed (scatterometry or imaging). In such instances, the metrology system may be configured to switch the objective lenses between different types of measurements and at the same time to select either passively or actively two separate optical subassemblies in the rest of the optical elements. Alternatively, if the metrology system includes two such separate objective lenses, the metrology system may be configured such that the objective lenses (and the corresponding optical elements) are stationary. In such instances, the metrology system may include two fixed and stationary optical columns (one column for each objective lens and its corresponding optical elements), and the metrology system may be configured to move the wafer such that the metrology target is moved from the field of view of one optical column to the other depending on the measurements to be performed on the wafer.

The computer system may be configured to determine the characteristic of the grating target by accounting for effects of the field stop on the output. For example, the computer system may be configured to use algorithms to account for the change of the signal scattered from the wafer by the relatively small collection field stop. In addition, the embodiments described herein may combine an apodizer, collection field stop, and algorithms to account for the change in the scattered intensity due to the collection field stop for CD and overlay metrology.

As described above, the metrology system may be configured to perform ellipsometry measurements of the wafer. In one such embodiment, the computer system is configured to determine a characteristic of a film formed on the wafer using output generated by the detector during the ellipsometry measurements. The characteristic of the film may include, for example, film thickness, refractive index, and any other thin film characteristic that can be determined used ellipsometry measurements. The computer system may be configured to determine the characteristic of the film in any suitable manner. For example, the computer system may be configured to determine film and other characteristics using ellipsometry measurements as described in commonly owned U.S. Pat. No. 7,515,253 to Bareket et al., which is incorporated by reference as if fully set forth herein. In addition, the computer system may be configured to determine a characteristic of the film using spectroscopic scatterometry measurements of the film. Such an embodiment may be combined with any other embodiments described herein. For example, one embodiment of the metrology system may include a combination on the same platform of an optical CD metrology system, a scatterometry and imaging overlay metrology system and a film metrology system. In addition, as described above, the metrology system may be integrated into a semiconductor fabrication system. In this manner, the metrology system may be used as a single integratable sensor for a lithography system, which can be used to measure scatterometry overlay, CD, film thickness, and UV two-beam imaging overlay. Such a metrology system would meet the 16 nm technology node requirements.

One advantage of the embodiments described herein is that the metrology system can be configured and used as a multifunction metrology system. For example, the metrology system is configured to provide on a single platform a combination of different applications. In this manner, the metrology system can be configured to determine more than one characteristic of the grating target or other structures (features) on the wafer using one or more of the techniques described herein. In other words, multiple metrology tasks can be performed by a suitable selection or combination of different metrology methods such as scatterometry and imaging methods. In one such example, the computer system may determine a CD of patterned structures in the grating target as described above using scatterometry measurements performed using the metrology system and overlay of the patterned structures with respect to other patterned structures using the scatterometry measurements, other scatterometry measurements performed using the metrology system, or imaging performed using the metrology system. In another example, the computer system may determine the CD using the scatterometry measurements, the overlay using the scatterometry measurements or the imaging results, and a thin film characteristic using the ellipsometry measurements. In this manner, the embodiments described herein may combine in one metrology tool the following metrology tasks: optical CD metrology, optical overlay metrology, and film metrology. In addition, the computer system may determine any other combination of characteristics described herein using any combination of techniques described herein.

In some embodiments, the optical elements are configured to direct the scattered light that passes through the field stop to only a first portion of the detector. In one such embodiment, the optical elements are configured to direct a portion of the diffraction-limited light beam to only a second portion of the detector without first directing the portion of the diffraction-limited light beam to the wafer, and the second portion of the detector does not overlap with the first portion of the detector. For example, the metrology system may perform a method for measuring and optionally calibrating, suppressing, and eliminating spatially correlated, noise, in which a reference part of the light from the light source is directed to a part of the metrology detector (e.g., CCD or camera), without overlapping with the metrology signal. The reference part of the light source preferably uses the maximum possible common path with the actual signal path, without reflecting from the wafer. An advantageous feature of this calibration is that it can take place simultaneously with the signal collection and that it can be used for calibrating the signal collected in the same time interval as the calibration signal. In this manner, the metrology system may be configured to perform fast feedback to the light source for stabilizing its power and wavelength.

In another embodiment, the optical elements are configured to direct the scattered light that passes through the field stop to only a first portion of the detector, while a second portion of the detector sees no light. The output generated by only the second portion of the detector, which does not overlap with the first portion of the detector, is used by the computer system to calibrate the output generated by the detector that is responsive to the detected scattered light in the first portion of the detector. In this manner, part of the detector may be used for calibration. For example, the metrology system may be configured to perform a method for measuring and optionally calibrating, suppressing, and eliminating a spatially correlated part of dark noise utilizing a part of the metrology detector (e.g., CCD or camera) unexposed by any light in the system, for instance, unexposed by the signal itself, the above-described reference part of the illumination light beam, or any other light. An advantageous feature of this calibration is that it can take place simultaneously with the signal collection and that it is used for calibrating the signal collected in the same time interval as the calibration signal.

The embodiments described herein also provide an extendible metrology system platform to accommodate future requirements for the applications described herein. For example, as described above, the metrology system may include a visible light source. In this manner, the metrology measurements (e.g., angle-resolved scatterometry) may be performed in the visible spectral region. However, the operation of the angle-resolved scatterometer can be extended into the spectral region of near-UV or deep-UV. Operation in such a spectral region will impose additional requirements on all of the optical components, but specifically on the objective lens. In addition, the metrology system is configurable (e.g., integratable, combinable with other commercially available metrology systems such as the Archer 300 series of tools that are commercially available from KLA-Tencor, Milpitas, Calif., can be configured for imaging only, can be configured for scatterometry only, etc.). Furthermore, the metrology systems described herein are compatible with on-the-fly concepts (in this instance, measuring a target while it is moving) because the metrology systems may be configured to scan the illumination spot over grating targets.

Another embodiment relates to a metrology method. The metrology method includes shaping a diffraction-limited light beam in the entrance pupil of illumination optics in such a way that the irradiance farther than 1.5 microns from the center of an illumination spot in the wafer plane is less than $10^{-6}$ of the peak irradiance of the center of the spot. Shaping the diffraction-limited light beam in this manner may be performed as described further herein (e.g., using an apodizer as described further herein). The metrology method also includes directing the diffraction-limited light beam to the illumination spot on a grating target on a wafer. Directing the light beam to the illumination spot may be performed as described further herein (e.g., using optical elements described further herein). In addition, the metrology method includes collecting scattered light from the grating target. Collecting the scattered light from the grating target may be performed as described further herein (e.g., using optical elements described further herein). The metrology method further includes rejecting a portion of the collected scattered light from the grating target. Rejecting the portion of the collected scattered light may be performed as described further herein (e.g., using a field stop configured as described herein). The metrology method also includes detecting the scattered light subsequent to rejecting the portion of the collected scattered light. In addition, the metrology method includes generating output responsive to the detected scattered light. Detecting the scattered light and generating the output may be performed as described further herein (e.g., using a detector configured as described herein). The metrology method further includes determining a characteristic of the grating target using the output. Determining the characteristic may be performed as described further herein (e.g., using a computer system configured as described herein).

The method may also include storing results of any of the step(s) of the method in a storage medium. The results may include any of the results described herein (e.g., a characteristic of a grating target) and may be stored in any manner known in the art. The storage medium may include any suitable storage medium known in the art. After the results have been stored, the results can be accessed in the storage medium and used as described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

The method described above may include any other step(s) of any method(s) described herein. In addition, the method described above may be performed by any metrology system embodiments described herein.

Further modifications and alternative embodiments of various aspects of the invention will be apparent to those skilled in the art in view of this description. For example, metrology systems and methods are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A metrology system, comprising:
   a light source configured to produce a diffraction-limited light beam;
   an apodizer configured to shape the light beam in an entrance pupil of illumination optics in such a way that an irradiance farther than 1.5 microns from the center of an illumination spot in a wafer plane is less than $10^{-6}$ of the peak irradiance of the center of the spot;
   optical elements configured to direct the diffraction-limited light beam from the apodizer to the illumination spot on a grating target on a wafer and to collect scattered light from the grating target;
   a field stop configured to reject a portion of the collected scattered light;
   a detector configured to detect the scattered light that passes through the field stop and to generate output responsive to the detected scattered light such that the grating target is measured by the metrology system using scatterometry; and
   a computer system configured to determine a characteristic of the grating target using the output.

2. The metrology system of claim 1, wherein the light source comprises a laser and a single-mode fiber.

3. The metrology system of claim 1, wherein the illumination spot on the grating target has a diameter that is less than 3 microns.

4. The metrology system of claim 1, wherein the grating target has lateral dimensions of less than 10 microns by less than 10 microns.

5. The metrology system of claim wherein the metrology system is configured to scan the illumination spot across the grating target while the scattered light from the grating target is being collected, 6. The metrology system of claim 1, wherein the scatterometry comprises angle-resolved scatterometry.

7. The metrology system of claim 1, wherein the scatterometry comprises angle-resolved scatterometry performed using multiple discrete wavelengths.

8. The metrology system of claim 1, wherein the scatterometry comprises spectroscopic scatterometry.

9. The metrology system of claim 1, wherein the scatterometry comprises spectroscopic scatterometry performed using multiple discrete angles.

10. The metrology system of claim 1, wherein the optical elements comprise a polarizer positioned in the path of the diffraction-limited light beam and an analyzer positioned in the path of the collected scattered light, and wherein the polarizer and analyzer are configured such that the scatterometry can be performed using multiple polarization states.

11. The metrology system of claim 1, wherein the field stop is not centered on an optical axis along which the collected scattered light travels to thereby reduce ghosting of the collected scattered light on the detector.

12. The metrology system of claim 1, wherein the optical elements are further configured to concentrate ghost images of the collected scattered light to localized areas in an imaging pupil of the optical elements or to spread the ghost images out across the imaging pupil to reduce irradiance of the ghost images.

13. The metrology system of claim 1, wherein the characteristic comprises critical dimension of patterned structures in the grating target.

14. The metrology system of claim 1, wherein the characteristic comprises overlay of patterned structures in the grating target with respect to patterned structures of another grating target formed on the wafer, and wherein the grating target and the other grating target are formed on different layers of the wafer.

15. The metrology system of claim 1, wherein the optical elements are further configured to direct the scattered light that passes through the field stop to only a first portion of the detector, wherein the optical elements are further configured to direct a portion of the diffraction-limited light beam to only a second portion of the detector without first directing the portion of the diffraction-limited light beam to the wafer, and wherein the second portion of the detector does not overlap with the first portion of the detector.

16. The metrology system of claim 1, wherein the optical elements are further configured to direct the scattered light that passes through the field stop to only a first portion of the detector, wherein a second portion of the detector sees no light, wherein output generated by only the second portion of the detector is used by the computer system to calibrate the output generated by the detector that is responsive to the detected scattered light in the first portion of the detector, and wherein the second portion of the detector does not overlap with the first portion of the detector.

17. The metrology system of claim 1, wherein the optical elements comprise a polarizer positioned in the path of the diffraction-limited light beam and an analyzer positioned in the path of the collected scattered light, and wherein the metrology system is configured to use at least the light source, the optical elements including the polarizer and the analyzer, and the detector to perform ellipsometry measurements of the wafer.

18. The metrology system of claim 1, further comprising an additional detector configured to generate an image of the wafer, wherein the computer system is further configured to determine an additional characteristic of the grating target using the image.

19. The metrology system of claim 17, wherein the computer system is further configured to determine a characteristic of a film formed on the wafer using output generated by the detector during the ellipsometry measurements.

20. The metrology system of claim 18, wherein the characteristic comprises scatterometry-based overlay, and wherein the additional characteristic comprises imaging-based overlay.

21. The metrology system of claim 18, wherein the optical elements comprise an objective lens configured to collect the scattered light from the grating target and configured to collect light from the wafer used to generate the image.

22. A metrology method, comprising:
shaping a diffraction-limited light beam in an entrance pupil of illumination optics in such a way that an irradiance farther than 1.5 microns from the center of an illumination spot in a wafer plane is less than $10_{-6}$ of the peak irradiance of the center of the spot;
directing the diffraction-limited light beam to the illumination spot on a grating target on a wafer;
collecting scattered light from the grating target;
rejecting a portion of the collected scattered light from the grating target with a field stop;
detecting the scattered light subsequent to said rejecting;
generating output responsive to the detected scattered light, wherein said detecting and said generating are performed with a detector configured to detect the scattered light that passes through the field stop and to generate the output responsive to the detected scattered light such that the grating target is measured by the metrology method using scatterometry; and
determining a characteristic of the grating target using the output.

* * * * *